(12) United States Patent
Pan et al.

(10) Patent No.: US 8,097,259 B2
(45) Date of Patent: Jan. 17, 2012

(54) METHOD FOR PREVENTION AND TREATMENT OF ALZHEIMER'S DISEASE

(75) Inventors: Tzu-Ming Pan, Taipei (TW); Chun-Lin Lee, Taipei (TW)

(73) Assignee: SunWay Biotech Co., Ltd., Taipei (TW)

( * ) Notice: Subject to any disclaimer, the term of this patent is extended or adjusted under 35 U.S.C. 154(b) by 0 days.

(21) Appl. No.: 12/723,966

(22) Filed: Mar. 15, 2010

(65) Prior Publication Data

US 2010/0221239 A1 Sep. 2, 2010

Related U.S. Application Data

(63) Continuation-in-part of application No. 11/963,533, filed on Dec. 21, 2007, now abandoned.

(51) Int. Cl.
*A61K 36/06* (2006.01)
(52) U.S. Cl. .............. 424/195.16; 424/115; 435/256.8
(58) Field of Classification Search .......... None
See application file for complete search history.

(56) References Cited

U.S. PATENT DOCUMENTS

2004/0081663 A1* 4/2004 Chang et al. ............. 424/195.16

OTHER PUBLICATIONS

Coley et al. (Epidem. Rev. (2008), vol. 30, pp. 35-66, especially p. 56 "Conclusion")).*
Fillit (Alzheimer's & Dementia (2008), vol. 4, pp. S26-S28).*
Lee (Appl. Microbiol. Biotechnol. (Mar. 2006), vol. 72, pp. 1254-1262).*
Tortora (Microbiology: An Introduction (2004), Benjamin Cummings: San Francisco, pp. 803).*

* cited by examiner

*Primary Examiner* — Susan Hoffman
(74) *Attorney, Agent, or Firm* — Anova Law Group, PLLC; Wenye Tan

(57) ABSTRACT

This invention provides method for the treatment and prevention of Alzheimer's disease without noticeable side effects caused to patients, comprising administering an effective amount of *Monascus*-fermented product including *Monascus* powder and *Monascus* beverage. The *Monascus* powder and beverage are prepared through specific fermentation procedures disclosed and comprise monacolins, anti-inflammation agents and anti-oxidant compounds. The *Monascus* compositions are extracted from fermented red mold rice (RMR).

10 Claims, 21 Drawing Sheets

METHOD FOR PREVENTION AND TREATMENT OF ALZHEIMER'S DISEASE

REFERENCE TO RELATED APPLICATIONS

This application is a continuation-in-part of U.S. patent application Ser. No. 11/963,533 filed on Dec. 21, 2007, now abandoned, and published as U.S. Patent Application Publication No. 20090162456A1 on Jun. 25, 2009.

The above referenced application, and each document cited or referenced in the above referenced application, are hereby fully incorporated by reference herein.

TECHNICAL FIELD

The present invention relates to the prevention and treatment of Alzheimer's disease, in particular, to method for the prevention and treatment of Alzheimer's disease in mammals comprising administering to the mammal an effective amount of *Monascus*-fermented product including *Monascus* powder and *Monascus* beverage, said powder or beverage comprising monacolins, anti-inflammation agents and anti-oxidant compounds that are extracted from fermented red mold rice (RMR).

BACKGROUND OF THE INVENTION

Alzheimer's disease (AD) is associated with a progressive neurons failure. AD is a major cause of dementia, most often dementia and AD are used interchangeably. In Alzheimer's disease (AD), the progressive loss of cognitive, language and emotional functions occurs. Generally, serious AD patients need more care and require assistance in all respects, such as taking a bath, eating, going to the bathroom, etc. Therefore, there are great impacts on the families of those AD patients in their daily lives. Loss of memory is the most often seen symptom of AD. At the very beginning, the symptoms such as memory loss are often mistakenly thought by the family members of AD patients as "age-related." But a physician can diagnose the disease with cognitive tests and brain scan. Some known symptoms that seriously affects a person's ability to carry out his/her daily activities include no recognition of a place or direction, loss of memory of recent events, bringing up matters of the past repeatedly, or unable to learn new things. As the disease gets worse, patients often have difficulty in expressing himself/herself or making decisions. Gradually, AD patients may lose the ability to recognize family members and relatives. Some AD patients may suffer confusion, agitation, paranoia, mood swings, language breakdown, and general withdrawal. New studies show that the brain damages of AD patients involve the human vision and sense of space. Thus, an AD patient often has problem in identifying a direction or finding his/her way. AD patients may wander on the streets as they forget their destinations or cannot find their way home. At home, AD patients may gradually lose bodily functions, thus have difficulty in carrying out daily activities by themselves. Other damages to the brain cells of AD patients, e.g., the basal forebrain and hippocampus, may lead to long-term memory loss and confusion. Many AD patients eventually die from the disease, or from other causes related to their lifestyle change such as pneumonia. Generally, AD patients can live 6-8 years, but many AD patients can survive for more than 20 years, putting severe burden on their families and society.

The Food and Drug Administration (FDA) of the United States has approved five pharmaceutical treatments for Alzheimer's disease in clinical use, including the cholinesterase inhibitors such as Tacrine and Donepezil. Cholinesterase is an enzyme that catalyzes the hydrolysis of neurotransmitter acetylcholine (AChE) into choline and acetic acid. Those aforementioned approved pharmaceuticals can inhibit cholinesterase and repress the hydrolysis of neurotransmitter acetylcholine (AChE). Consequently, both Tacrine and Donepezil can be used to increase the AChE content in human brain, which in turn may defer the process of memory-loss, and may allow AD patients to continually carry out their daily activities Importantly, those pharmaceutical treatments are unable to cure Alzheimer's disease, but only relieve certain AD symptoms. Moreover, the aforementioned medications have been proved to carry side effects to AD patients, including nausea, headache, diarrhea, insomnia, pain, illusion and dizziness, etc. Therefore, new method for the prevention and treatment of Alzheimer's disease without noticeable side effects are desperately needed.

SUMMARY OF THE INVENTION

A primary objective of the present invention is to provide method for the treatment and prevention of Alzheimer's disease without noticeable side effects to patients.

Another objective of the invention is to provide a method for the prevention and treatment of Alzheimer's disease without noticeable side effects caused to AD patients, comprising administering to the mammal an effective amount of *Monascus*-fermented product including *Monascus* powder and *Monascus* beverage.

Another objective of the invention is to provide a method for the preparation of the aforementioned *Monascus* powder or beverage from specific procedure comprising fermentation of rice.

Another objective of the invention is to provide a method for the preparation of the aforementioned *Monascus* product comprising one or more monacolins, one or more anti-inflammation agents and one or more anti-oxidant compounds.

Another objective of the invention is to provide a method of preventing or treating Alzheimer's disease by administrating to a mammal a composition extracted from red mold rice comprising one or more monacolins, one or more anti-inflammation agents, and one or more anti-oxidant compounds.

Another objective of the invention is to provide a method of preventing or treating Alzheimer's disease by administrating to a mammal a composition for the prevention and treatment of Alzheimer's disease, comprising one or more monacolins and one or more anti-inflammation agents.

The present invention discloses compositions for the prevention and treatment of Alzheimer's disease, said compositions comprising monacolins, anti-inflammation agents and anti-oxidant compounds, applied in various forms of pastils, capsules, powder, beverage, etc. in the prevention and treatment of Alzheimer's disease. The compositions of the invention, which are formed by the aforementioned three compounds, are used for the prevention and treatment of Alzheimer's disease.

An unrestricted deposit of the *Monascus purpureus* organism, which is disclosed and applied in the present invention, was made with the Agricultural Research Service Culture Collection (NRRL), located at 1815 N. University Street, Peoria, Ill. 61604, U.S.A., on Nov. 13, 2009, under Accession No. NRRL 50338. The deposit has been accepted under the Budapest Treaty. All restrictions on the availability of progeny of the strain to the public will be irrevocably removed upon the granting of a patent of which the strain is a subject.

The effects of *Monascus*-fermented product for the prevention of Alzheimer's disease, as well as for treatments of Alzhimer's disease at different stages, were further examined by feeding the products to groups of rats at different time periods before, during, and after infusion of Aβ40. The feeding of *Monascus*-fermented product to the "prevention" group of rats started 14 days before the Aβ40 infusion. Feedings to other groups of rats started later to simulate short-term treatments, early-stage treatments, late-stage treatments, and the no-treatment control group. Evaluation and comparison of the memory and learning abilities for rats in different groups were conducted by using the water maze and passive avoidance tasks. In addition, after sacrifice, the cerebral cortex and hippocampus were collected for examination. Those results indicate positive correlations between the length of feeding time (in days) and the rats' memory and learning abilities, as well as positive correlations between the length of feeding time (in days) and the decrease of Aβ40 accumulation in brain.

Moreover, in a preferred embodiment of the invention, the minimum content of monacolins is at least greater than 100 μg, the minimum content of anti-oxidant compounds is at least greater than 40 μg and the minimum content of anti-inflammation agents is at least greater than 10 μg; wherein the monacolines, anti-inflammation agents and anti-oxidant compounds have the optimum weight ratio of 40:2:1, enabling the composition of the invention to achieve the objectives of the prevention and treatment of Alzheimer's disease without causing noticeable side effects to AD patients.

Moreover, the invention discloses compositions for the prevention and treatment of Alzheimer's disease, the compositions comprising monacolins, anti-inflammation agents, wherein the minimum content of monacolins is at least greater than 200 μg and the minimum content of anti-inflammation agents is at least greater than 60 μg, wherein the monacolines and anti-inflammation agents have the optimum weight ratio of 10:1, enabling the composition of the invention to achieve the objectives of the prevention and treatment of Alzheimer's disease without causing noticeable side effects to AD patients.

Moreover, the present invention also discloses method for the treatment of Alzheimer's disease, the method comprises the following steps:

The first step is to rinse rice and carry out sterilization under a high pressure and high temperature environment, and then the second step is to cultivate a specific *Monascus purpureus* in fresh media under a first specific temperature, humidified and a specific shaking environment during a first specific timeframe, subsequently, the third step is to stir the media under the first specific temperature environment and provide a specific percentage of water during a second specific timeframe, the following step is to properly stir the media during a third specific timeframe under the first specific temperature environment at fixed intervals for afterripening, subsequently, after fermentation, the step is to collect a *Monascus*-fermented product and dry the product under a fourth specific timeframe at a second specific temperature, the next step is to grind the dried *Monascus*-fermented product into powder and analyze if the *Monascus*-fermented product conforms to a proportion of composition required, when the *Monascus*-fermented powder conforms to the proportion of composition required in the invention for the treatment of AD, the final step is to dissolve the *Monascus*-fermented powder in water in a specific proportion to make *Monascus* beverages or fill the *Monascus*-fermented powder in a capsule or make the the *Monascus*-fermented powder a pastil with effect on AD treatment. The method of the invention enables the *Monascus* composition to effectively achieve the treatment of AD without noticeable side effects caused to AD patients.

A detailed description is given in the following embodiments with reference to the accompanying drawings. Advantages and features of the present invention will become more apparent from the following detailed description of the present invention when viewed in conjunction with the drawings.

BRIEF DESCRIPTION OF THE DRAWINGS

FIGS. 12-1~12-3 are flowcharts showing the method of making the composition of the invention for the treatment of AD patients.

DETAILED DESCRIPTION OF THE PREFERRED EMBODIMENT

Figure 1:
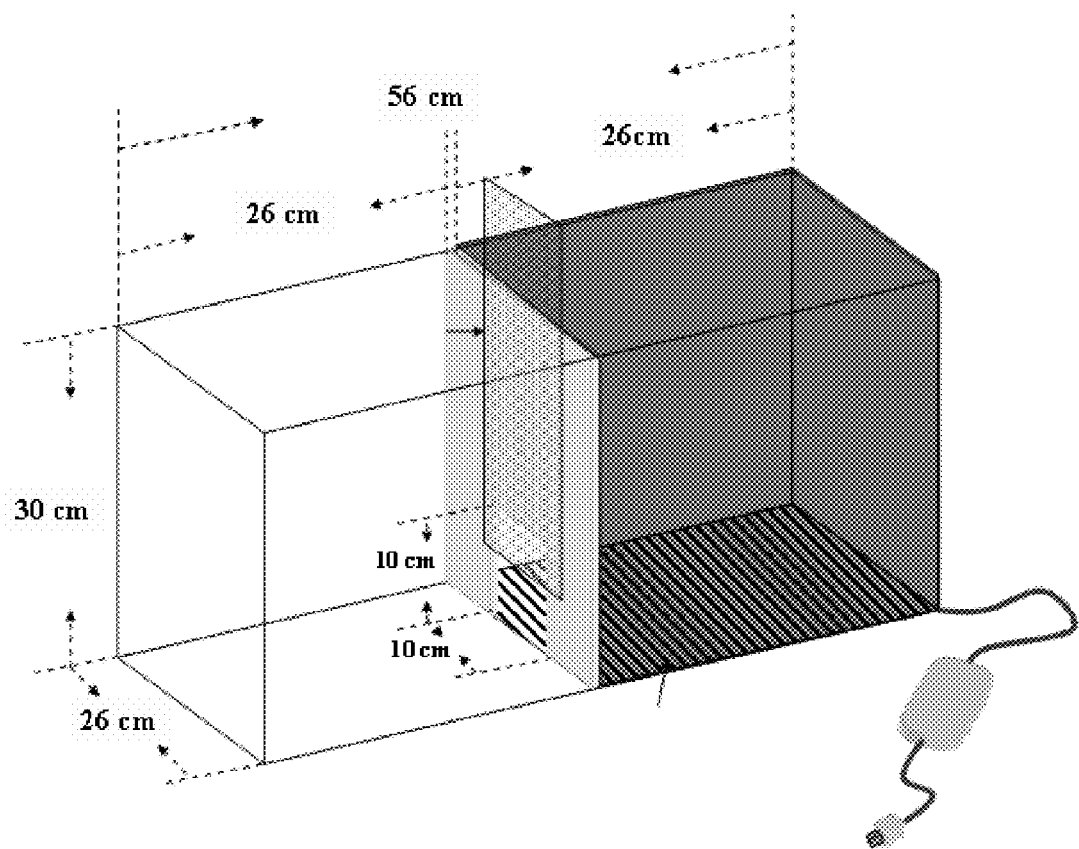
FIG. 1 is a prospective view of an apparatus according to the invention.

The invention discloses method and compositions for the prevention and treatment of Alzheimer's disease without causing noticeable side effects.

To help enable the general public to understand the disclosed present invention, an unrestricted deposit of the *Monascus purpureus* organism, which is disclosed and applied in the present invention, was made with the Agricultural Research Service Culture Collection (NRRL), located at 1815 N. University Street, Peoria, Ill. 61604, U.S.A., on Nov. 13, 2009, under Accession No. NRRL 50338. The deposit has been accepted under the Budapest Treaty. All restrictions on the availability of progeny of the strain to the public will be irrevocably removed upon the granting of a patent of which said *Monascus purpureus* strain is a subject.

Prior to introduction to the method and composition of the invention, some concepts of the invention are described as follows. Agitation and accumulation of Amyloid β peptide (Aβ) is the pathogenic agent of Alzheimer's disease (AD), leads to neurotransmitter deficits and repress oxidization and inflammatory response in the brain resulting in the aggravation of the AD situation for AD patients. Aβ is formed after sequential cleavage of the amyloid precursor protein (APP) through α, β and γ-secretase.

The formation of Aβ is carried out by the proteolytic cleavage of 671 and 672 amino acid binding site performed by β-secretase, as well as the cleavage of 713 amino acid binding site of APP performed by γ-secretase. The cleavage performed by secretase results in not only 1-40 and 1-42 fragment but also other fragment. APP would be cleaved in sAPP-α and p10 fragments by α-secretase. However, p10 would be further cleaved to p3, a part of Aβ, and p7 fragments. Furthermore, the cleavage of APP performed by β-secretase would result in the formation of sAPPβ and p12 fragments, and further cause p12 fragment to be cleaved to Aβ and p7 fragments though γ-secretase (Evin et al. 2003; Shoji et al. 1992). APP is cleaved to various types of Aβ though β- and γ-secretase. However, soluble Aβ without neurotoxicity would be aggregated as Aβ fibrils with neurotoxicity which leads to neuron damage via the balance disorder of calcium ion and oxidative stress. Aβ fibrils also break neurite outgrowth and cell death though promoting hyperphosphorylation of tau protein.

In addition, Aβ fibrils would bind to the specific receptor on the membrane of microglia and astrocyte, which leads to the activation of microglia involved in the release of many neurotoxic factors such as proinflammatory factors: IL-6, IL-1, and TNF-α as well as NO, ROS, and free radical. Currently, Apolipoprotein E gene in the 19th pair of chromosome is found to associate with AD pathogenesis. ApoE is able to easily and rapidly bind to Aβ, and further result in the deposition of senile plaque involved in neurotoxicity. In addition, many documents and literatures indicate that there is a certain relation between cardiovascular disease and Alzheimer's disease. Researches by Martha et al focused their experiments on elders above 65 years old and elucidated the results that those elders who ingested saturated fats during their diet easily have cardiovascular disease and most of those elders suffered from Alzheimer's disease 4 years on average after they were with diagnosed cardiovascular disease; in contrast, there was an inverse correlation if those elders whose diet contained abundant polyunsaturated fat and monounsaturated fat (Freund-Levi et al. 2006). Many researches have proved that there is a relation between Aβ production, which promotes Alzheimer's disease, and intracellular lipid metabolism (Frears et al. 1999; Kuo et al. 1998; Roher and Kuo 1999). Recent researches have found that Aβ alters due to intracellular cholesterol distribution and cholesterol esterification (Frears et al. 1999). ApoE increases plasma cholesterol levels and is one of the risk factors associate with cardiovascular disease. The experiment (Puglielli et al. 2001) showed that there is a positive correlation between acetylcholinesterase (AChE) activity and cholesterol ester (CE) content in the rat cells (Puglielli et al. 2001; Zhao et al. 2005). Therefore, it is found from researches that there is a positive correlation between cardiovascular disease and Alzheimer's disease.

Consequently, the compositions of the invention are used to decrease the Aβ accumulation in the brain and reduce saturated fats which may contribute to cardiovascular disease, so as to remedy Alzheimer's disease.

In recent year, there are many researches associated with *Monascus* species. In the future, the development of RMR ingredients and compounds may become part of health food with multi-functions for human beings. The invention proves that monacolin K, γ-aminobutyric acid (GABA) and antioxidant compounds in RMR are substantially enhance the feasibility for the treatment of Alzheimer's disease.

Monacolin K is lovastatin, a 3-hydroxy-3-methylglutaryl-coenzyme A (HMG CoA) reductase inhibitor (statin) for lowering cholesterol levels, and is clinically proved to effectively improve the symptoms of cardiovascular disease (CAD). In recent years, researches in epidemiology have found that statin has great clinical effectiveness for treatment of Alzheimer's disease. In UK General Practitioners Research Database that recent clinical reports describe an association between statin therapy and a reduction in the occurrence of Alzheimer's disease by as much as 70% (Jick et al. 2000). Similar researches include an experiment that focused on AD patients above 60 years old in three hospitals in the USA, their AD diagnosis is based on the standard of National Institute of Neurological and Communicative Disorders and Stroke and the Alzheimer's Disease and Related Disorders Association (NINCDS-ADRDA). The experiment divided those AD patients into three groups, group A was a control group, group B was remedied by statins, group C was remedied by other cardiovascular disease medications (including medicine for lowering blood pressure), the experiment results showed surprisingly that the group of AD patients with statins remedy enabled the AD levels to decrease 70%, wherein the lovastatin and pravastatin had the best results for AD treatment (Wolozin et al. 2000).

Nerve impulse transmission agents, including nicotinic, muscarinic, serotonin, glutamate receptor and γ-aminobutyric acid (GABA), norepinephrine in the brain of AD patients are damaged. During aging process, human brain volumn will reduce 10%, mainly the quantity of cerebral cortex neuron, some brain area quantity will reduce 30-50% of volumn and neurotransmitters are also reduced, such as AChE, GABA, catecholamine, etc. In view of the foregoing, AD patients will gradually lose their brain cognition or memory ability. AD symptoms in early stage include memory deficit, confusion, or difficulty making decisions. In later AD period, patients have the symptoms of language disorder, abnormal behaviors, spasm, unable to carry out daily activities (Mohr et al. 1994).

When $O_2$ or $H_2O_2$ is deficient and OH. is excessive in mitochondria, OH. is formed with high response. Oxidative free radicals enable A$\beta$ to form insolubile A$\beta$, and worsen AD symptoms (Hsieh and Tai 2003). It is found from experiment results that oral anti-oxidants such as a combination preparation comprising vitamin C and vitamin E is able to effectively alleviate AD symptoms (Yallampalli et al. 1998; Yamada et al. 1999). Ceramlde, a natural neurilemma, is used to against neuronal damage led by A$\beta$ and $FeSO_4$ in hippocampus (Abousalham et al. 2002). In 1999, Aniya et al proposed the anti-oxidation ability of *Monascus* that anti-oxidant mechanism of dimerumic acid in *Monascus* is known to be able to eliminate the inhibition of LPO by .OH, .$O^{2-}$, ferryl-Mb and peroxyl radicals; *Monascus* provides an electron for oxide to oxidize itself into nitroxide radical, and then nitroxide radical scavenging will lead to an anti-oxidant effect (Taira et al. 2002). Anti-oxidant effect from RMR is applicable to prevention of Alzheimer's disease, so that AD patients' condition can be improved without being aggravated due to free-radical induced oxidation.

Part of this invention was disclosed on 30 Jul. 2007 in the Journal of Neuroscience Research (Lee C L, Kuo T F, Wang J J, Pan T M: Red mold rice ameliorates impairment of memory and learning ability in intracerebroventricular amyloid beta-infused rat via repressing amyloid beta accumulation. J. Neurosci Res. 2007, 85, 3171-3182). In the experiment of the invention, male Wistar rats (weighing 250 g, 8 weeks old) were obtained from the Laboratory Animal Center of National Taiwan University College of Medicine. They were divided into 7 rats per group and kept in a temperature-controlled room (23±1° C.) under a 12-hr light: 12-hr dark cycle (light on at 08:00 and off at 20:00) and were given free access to food and water. When the weight is approximately 300 g, those rats were divided into groups with brain infusion. The daily RMR dietary and A$\beta$40 infusion are as shown in Table 1. The rats were divided to groups including 1) vehicle infused rats (vehicle group), surgery for i.c.v. with vehicle solution; 2) A$\beta$40 infused (A$\beta$ group), which were infused i.c.v. with A$\beta$40 solution; 3) A$\beta$40 infused with administration of lovastatin (LS group), 4) A$\beta$40 infused with administration of a onefold dosage of RMR (RL group) and 5) A$\beta$40 infused with administration of a fivefold dosage of RMR (RH group). The dosage of RMR is calculated in accordance with Boyd's formula of body surface area as recommended by the Food and Drug Administration (Boyd 1935; Lee et al. 2006). 2 g of RMR was used as the onefold dosage for an adult with a weight of 65 kg and a height of 170 cm. RH group of rats were daily administered high dosage of RMR, LS and RL groups of rats were administered the same dosage of lovastatin (1.43 mg/kg/day, per rat) for comparing the effects between applying simply monacolin K and applying RMR composition, including comprising monacolins, anti-inflammation agents and anti-oxidant compounds, for the treatment of AD.

Rats were injected with A$\beta$40 infusion for 28 consecutive days in the brain to develop Alzheimer's disease. The daily dietary dose of RMR products or the same lovastatin contents was used for those rats to find out the RMR outcome against A$\beta$-induced neurotoxicity and evaluate effect of RMR on the memory and learning ability of the rats. The results of the experiment of the invention show that infusion of A$\beta$40 for 28 consecutive days in the brain increased the AChE activity, reactive oxygen species (ROS) content, and lipid peroxide (LPO) levels, and at the same time reduce Total antioxidant capacity (T-AOC) and superoxide dismutase (SOD) activity. The dietary dose of RMR significantly repressed the A$\beta$40 infusion damage to the brain and had better effect compared with lovastatin group. Moreover, A$\beta$40 infusion was not able to considerably accumulate in hippocampus through repressing oxidation and inflammatory response. Red mold rice (RMR) is at the first time proved to have the effect on decreasing the risk factor for memory deficit and dementia in AD patients and the effects is significant compared with lovastatin group.

The animals grouping and experiment schedule of the invention are as follows:

TABLE 1

| Groups | A$\beta$ Infusion | RMR (monacolin K) (mg/kg rat per day) | Lovastatin (mg/kg rat per day) |
|---|---|---|---|
| Vehicle | — | — | — |
| A$\beta$ | + | — | — |
| LS | + | — | 1.43 |
| RL | + | 151 (1.44) | — |
| RH | + | 755 (7.20) | — |

With reference to FIG. 1, an apparatus 10 consisted of a light chamber 11 and a dark chamber 12; the chambers were both the same size. A shuttle door 13 of 10 (W)×10 (D) cm was set for separation of the two chambers. When the shuttle door 13 was opened, the light chamber 11 and the dark chamber 12 are open to each other. The light chamber 11 is with illumination, whereas the dark chamber 12 is not. A plurality of electric wires 14 arranged with a parallel interval of 1 cm were set through the floor of the dark chamber 12 and delivered an electric shock when the door was closed. In each trial, a rat was placed into the light chamber 11 first and the shuttle door 13 was opened. After the rat entered the dark chamber 12, the shuttle door 13 was immediately closed and the retention time was recorded, and an inescapable electric shock (100 V, 0.3 mA, 2 sec) was delivered through the electric wires 14, the rat was removed from the dark chamber after 5 sec. of foot shock. If the rat was indifferent to go into the dark chamber 12 after 300 sec., the rat was compelled to go into the dark chamber 12 and received electric shock through the electric wires 14 arranged on the floor of the dark chamber 12 after the shuttle door 13 was closed. Subsequently, the rat was again placed into the light chamber 11 with the shuttle door 13 opened, and the step-through latency of the rat in the light chamber 11 was measured in the retention test performed 24 hours and 48 hours after the training trial. If the time the rat stayed in the light chamber 11 was measured above 300 sec., memory and learning ability of the rat was considered normal without problem.

Figure 2:
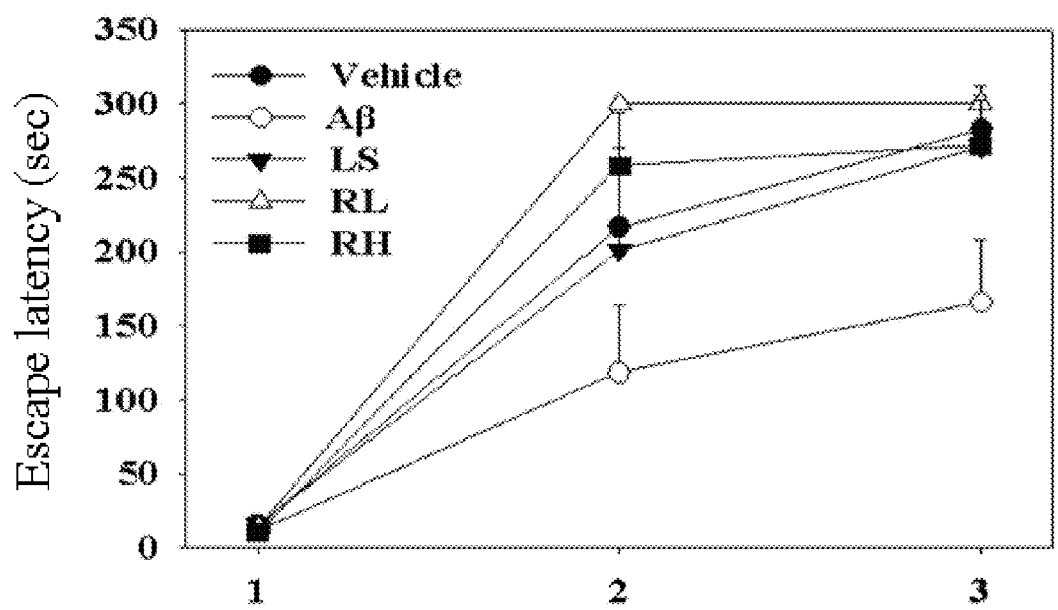
FIG. 2 is a statistical chart showing the effect of RMR on step-through latency of multiple-trial passive avoidance task in the rats from a light chamber into a dark chamber.

The step-through latency of a rat from the light chamber 11 to the dark chamber 12 was used as a marker to evaluate the memory and learning ability in the passive avoidance task. As shown in FIG. 2, all the rats would immediately go into the dark chamber 12 in the first trial because of skoto-taxis, but the electric shock in the dark chamber 12 should intimidate and prevent rats with normal memory ability from going into the dark chamber 12 the next time. Therefore, the step-through latency among each group of rats in the light chamber 11 would show the most significant difference in the second trial. The results of the second trial clearly indicate that Aβ-infused rats still spent shorter times staying in the light chamber than vehicle-infused rats. However, RL and RH groups are able to ensure staying in the light chamber for a longer time compared with the Aβ group (p<0.05). The effect on lovastatin group is lower than that on RL group with the same monacolin K contents, but the performance on the memory and learning ability improvement of lovastatin group is significantly higher than that of Aβ group.

Figure 3:
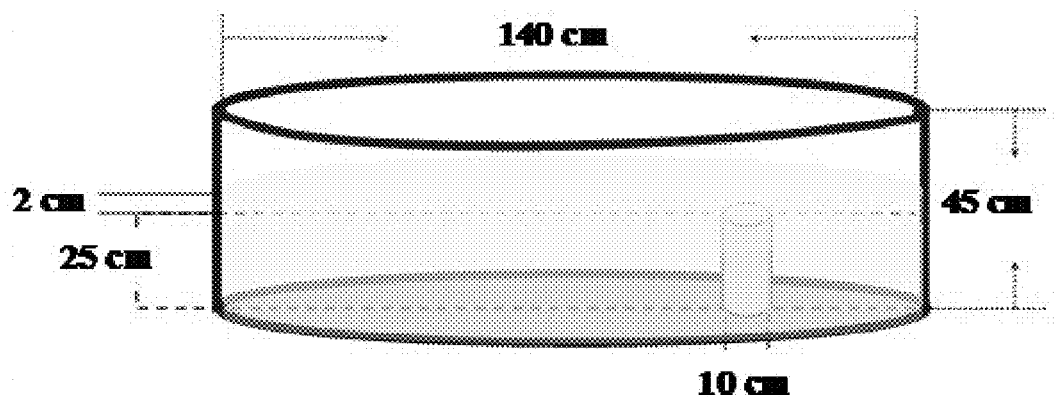
FIG. 3 shows perspective views regarding an apparatus of water maze according to the invention.
Figure 3:
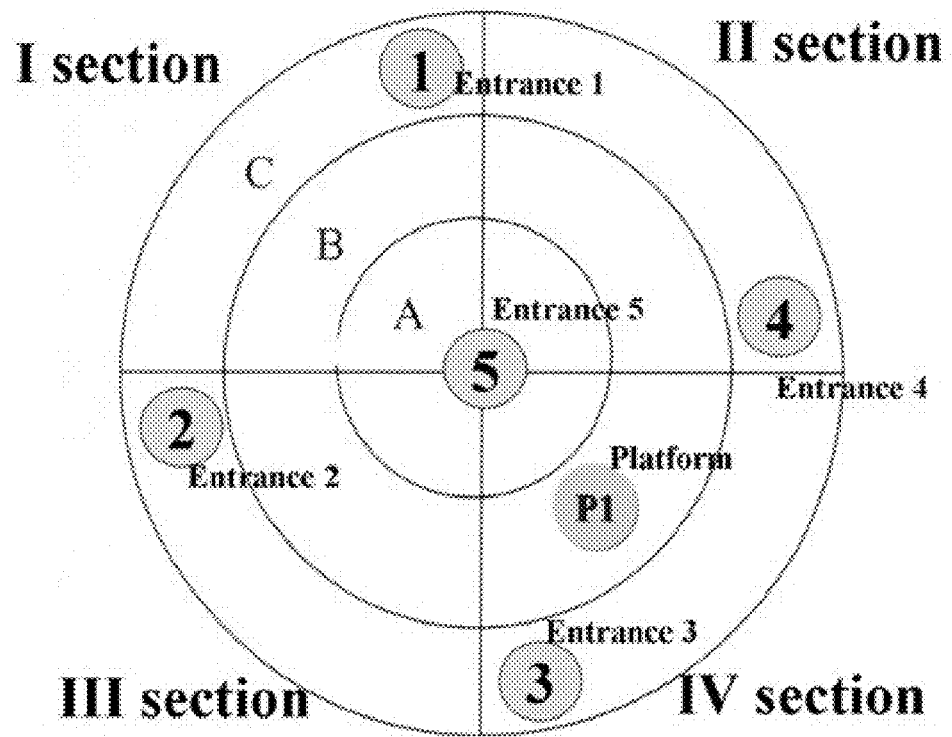

With reference to FIG. 3, the invention provides a water maze 20, comprising a circular tank 21 (diameter 140 cm, height 45 cm), which was used as an apparatus of the water maze 20 in which a movable escape platform P1 (diameter 12 cm, height 25 cm.) was located inside the tank 21. Prior to the experiment, the circular tank 21 was filled with water to a height of 27 cm. The circular tank 21 was divided into four quadrants (I, II, III and IV), there were five starting positions set in the tank 21 and a position with equal distance from center and edge in the middle of each quadrant was marked for the location of platform P1. During the experiment, a camera was set at the ceiling above the center of the water tank 21 for recording swimming routes of those rats.

Figure 4:
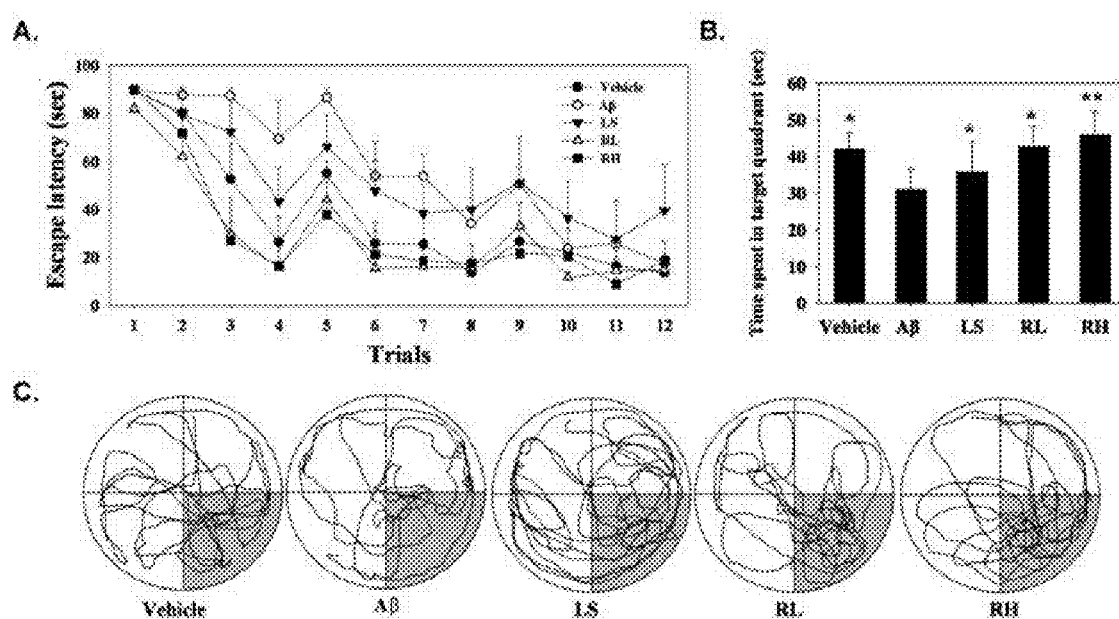
FIGS. 4-A, 4-B & 4-C show influence diagrams regarding effects of RMR on performance of the memory and learning ability of the Aβ40-infused rats in the training trials of reference memory task and probe test.

FIG. 4 shows the influence effects of RMR on performance of the memory and learning ability of the Aβ40-infused rats. The time that rats started from a starting point of the apparatus of water maze 20 to search the escape platform P1 is regarded as the index for evaluation of the reference memory task. The experiment results show that the Aβ-infused group always has longer escape latency of finding the escape platform P1 from the second trial to the ninth trial compared with the vehicle group. The dietary administration of RMR (RL and RH groups), however, significantly decreases escape latency from the second trial to the ninth trial compared with the Aβ-infused group (p<0.05). Lovastatin administration also results in shorter escape latency compared with the Aβ group, but the effect would be weaker than in the RL and RH groups. Changes in path length produced by training trials in each group of rats showed a pattern similar to that of escape latency. There also were no significant differences in swimming speed among those groups of animal during the course of the training trials (data not shown) (p>0.05).

Figure 5:
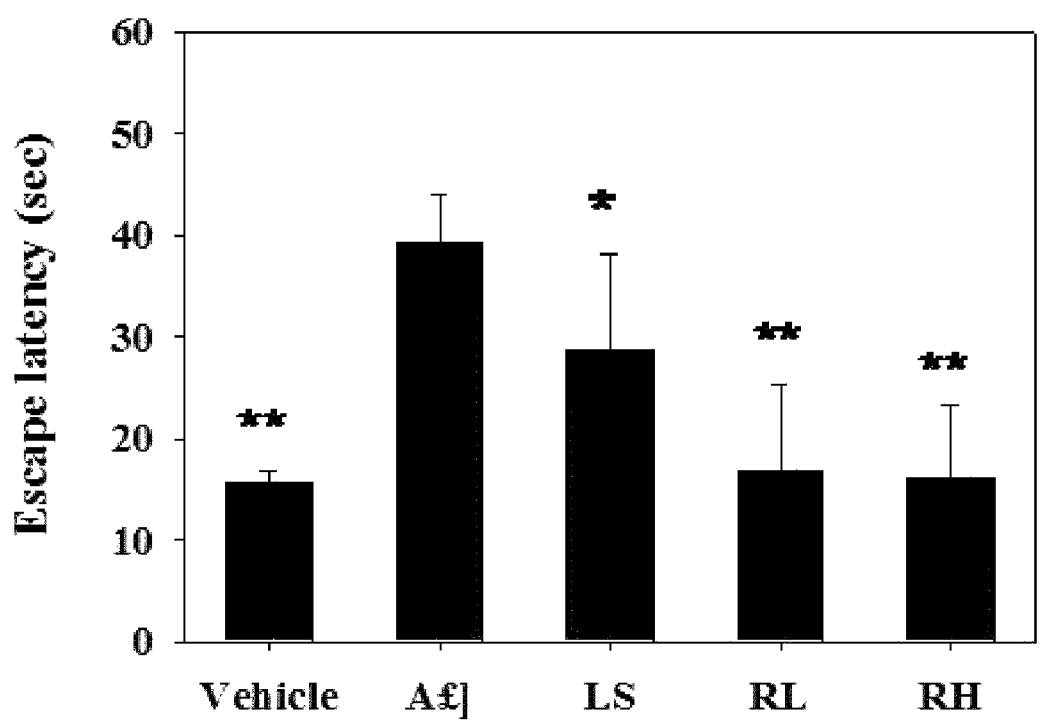
FIG. 5 is a chart showing effect of RMR on performance of the memory and learning ability of the Aβ40-infused rats in the training trials of working memory task.

Probe test was immediately carried out after the training trial of the last reference memory task on day 24. The escape platform P1 was removed from the apparatus of water maze 20 (water tank 21). The time that rats wandered in the original quadrant with the escape platform P1 placed therein is regarded as the index of the probe test for evaluation of the memory and learning ability. The results showed in FIG. 4-A that the Aβ group spent less time searching the target quadrant than the vehicle group (p<0.05). Administration with RMR at one-fold dosage in RL group or fivefold dosage in RH group results in significant increase on search time in the target quadrant by 38.2% (p<0.05) and 48.0% (p<0.01), respectively, compared with the Aβ group, suggesting that the increase in search time in the RL and RH groups is attributable to the effects of RMR. It proves that red mold rice is able to improve the memory and learning ability for AD. Swimming pathway is helpful in understanding the truth of the memory and learning ability of rats in spatial probe trial. FIG. 4-B clearly indicated that Aβ-infused rats searched the target quadrant with directionless escape and around the whole circular tank 21. In contrast, rats with better memory and learning ability, such as RL, RH and vehicle groups, swam directly to the target quadrant and lingered for a long time. However, the lovastatin group always resulted in an ordinary ameliorative effect between RL group and Aβgroup on impairment of memory and learning ability (FIGS. 4-B and 4-C). The working memory task is a method for evaluation of short-term the memory and learning ability. With reference to FIG. 5, Aβ-infused rats are unable to shorten the escape latency time in searching the escape platform P1 compared with vehicle group (p<0.01). However, both RL and RH groups are able to perform memory and learning as fast as the vehicle group in the working memory task, and RL and RH groups significantly decrease escape latency time by 57.3% and 58.9% compared with the Aβ group (p<0.01). LS group significantly decreases escape latency time by 26.7% compared with the Aβ group (p<0.05), but the effect was weaker than with the RL and RH groups (p<0.05).

Aβ has been proved to be the risk factor for memory deficit and dementia in AD patients (Hashimoto et al. 2005; Stephan and Phillips 2005) and intracerebroventricular (i.c.v.) infusion of Aβ40 into lateral ventricle of rats has been demonstrated as a successful method for establishing an AD animal model (Stephan and Phillips 2005). Learning ability and memory deficit were tested in the behavior of Aβ-infused AD rats (Kar et al. 1998; Schubert et al. 1995; Townsend and Pratico 2005). The free radials and ROS induced by Aβ deposit damaged the neuron and synaptic junction and finally led to memory deficit and lack of and learning ability (Townsend and Pratico 2005). Therefore, antioxidants and anti-inflammation agents have usually been tried to reduce these AD risk factors in brain and ameliorate the impairment of memory and learning ability (Chauhan et al. 2004; Cordle et al. 2005).

Morris water maze task is used to evaluate the memory and learning ability, the reference memory task is a method of evaluating long-term memory ability and the working memory task is a method of evaluating short-term memory ability. According to the results of the aforementioned memory and learning tasks, the AD rats with one-fold dosage and fivefold dosage of RMR shortened the escape latency time in the reference memory task and the working memory task (p<0.05). In addition, RMR dietary rats prolonged their searching time in the target wuadrant in probe trial. The experiment results clearly showed that rats with RMR dietary are able to improve the memory and learning ability to shorten the time in finding the escape platform in water maze. In contrast, AD rats without RMR dietary only searched the whole water maze with directionless escape and spent more time in the reference memory task and working memory task.

Monacolin K, an inhibitor of HMG-CoA reductase, was regarded as an important metabolite with hypolipidemic ability in RMR, statins are reported as a novel remedy for AD via the repression of Aβ formation and Aβ-induced inflammatory response (Chauhan et al. 2004; Li et al. 2006). Many studies related to AD have used statins to lower Aβ formation in an AD transgenic mouse model (Yamada et al. 1999). Lovastatin has never been used to ameliorate the impairment of memory and learning ability in the Aβ-infused AD rat model. In this study, lovastatin was used to substitute for monacolin K of RMR in order to investigate whether ameliorating the impairment of memory ability by RMR administration resulted only from monacolin K. The results on the memory task clarified that lovastatin results in a weaker effect on ameliorating the impairment of memory than in the RL group even though the two groups included equal levels of monacolin K or lovastatin. Therefore, monacolin K is not the only functional ingredient to ameliorate Aβ-induced memory impairment.

Figure 6:
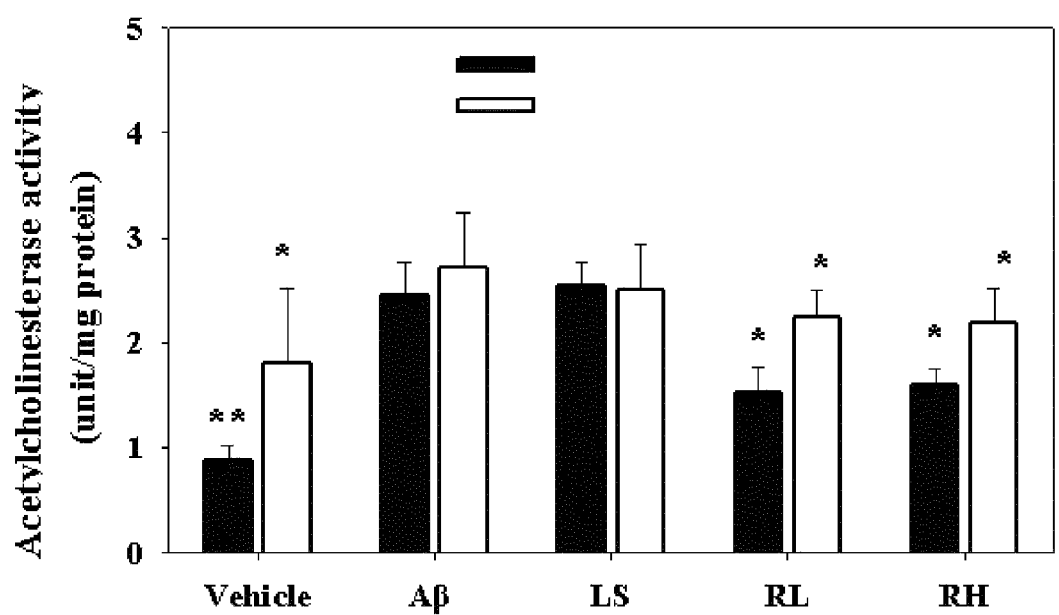
FIG. 6 is an influence diagram showing effect of RMR on activity of acetylcholinesterase (AChE) in the hippocampus and cortex of Aβ40-infused rats.

Currently, the treatment and remedy of AD mostly focus on inhibition of AChE activity to increase AChE concentration and improve brain cognition and memory ability (Nabeshima and Nitta 1994). Relevant researches by establishing AD animal model also proved that the neurotransmitter AChE in the brain would be significantly decreased in the Aβ-infused rats. Some researches also proved that Aβ-infused rats have substantially less AChE contents than normal rats (Arendt et al. 1984; Darvesh et al. 2004). The decrease in AChE concentration and an increase in AChE activity caused serious neuron loss (Stephan and Phillips 2005). In addition, the increase in AChE activity was proved to stimulate Aβ aggregation in vitro and to form stable complexes with Aβ fibrils (Stephan and Phillips 2005). Therefore, inhibition of AChE activity is regarded as neuro-protection mechanism to indirectly lower Aβ-induced memory deficit. FIG. 6 is an influence diagram showing effect of RMR on activity of acetylcholinesterase in the hippocampus and cortex of Aβ40-infused rats. Aβ i.c.v. infusion leads to an increase in AChE activity in cortex by 50.5% and by 179.1% in hippocampus compared with the vehicle group. Administration with onefold or fivefold dosages of RMR significantly inhibits the Aβ-increased AChE activity, but lovastatin is ineffective at inhibiting AChE activity in cortex and hippocampus. The results suggest that the ingredient in RMR with an inhibitory effect on Aβ-raised AChE activity should be not monacolin K but the other functional metabolites. Not many researches elucidated that lovastatin is able to inhibit AChE activity, even some researches pointed out that lovastatin does not have significantly inhibition effect on AChE activity. This research result matches the invention tendency. In addition to monacolin K, metabolite with effectiveness of RMR may include other AChE inhibitors. However, the metabolite, GABA of RMR, is also a neurotransmitter and is useful to improve cognition and memory ability of AD patients.

Figure 7:
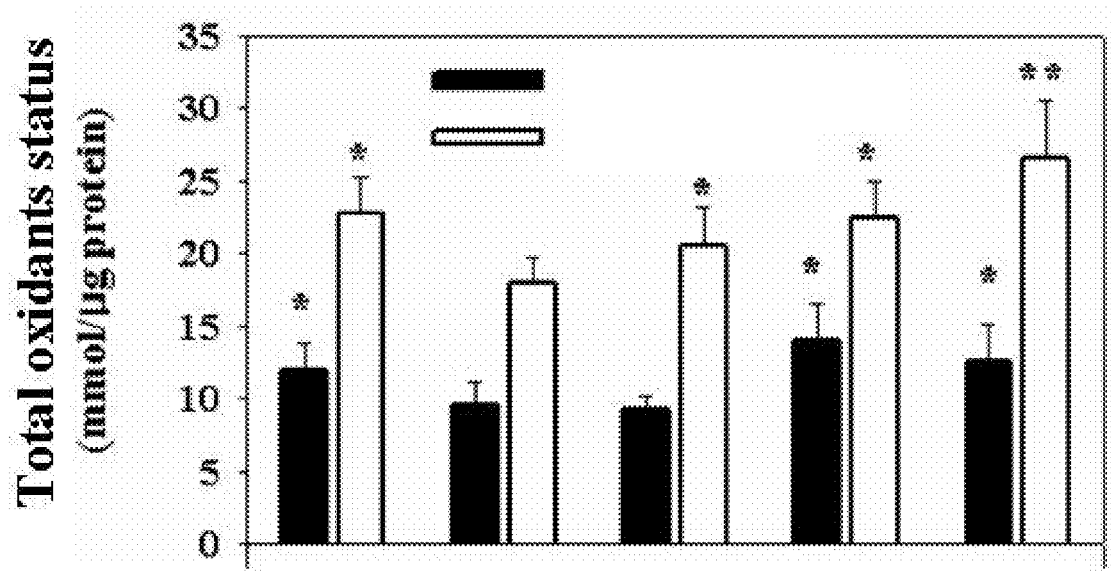
FIG. 7 is a schematic diagram showing effect of RMR on the formation of total antioxidant status (TAS) activity in the hippocampus and cortex of Aβ40-infused rats.

Aβ has been demonstrated to cause oxidative stress damage in AD brain. Therefore, repressing Aβ-induced oxidative stress was regarded as an important goal in drug development for AD. In FIG. 7, Aβ infusion decreases the total antioxidants status (TAS) levels of cortex and hippocampus by 20.9% and 20.4%, respectively, compared with the vehicle group. Lovastatin administration is able to increase TAS levels by 13.9% in cortex compared with the Aβ group, but it is ineffective in hippocampus. However, significant increases by 24.6% and 46.2% in TAS levels in cortex and hippocampus were seen in the RL group. However, the experiment results showed that fivefold dosage RMR is able to increase TAS levels in cortex and hippocampus in other groups compared with the Aβ group.

Figure 8:
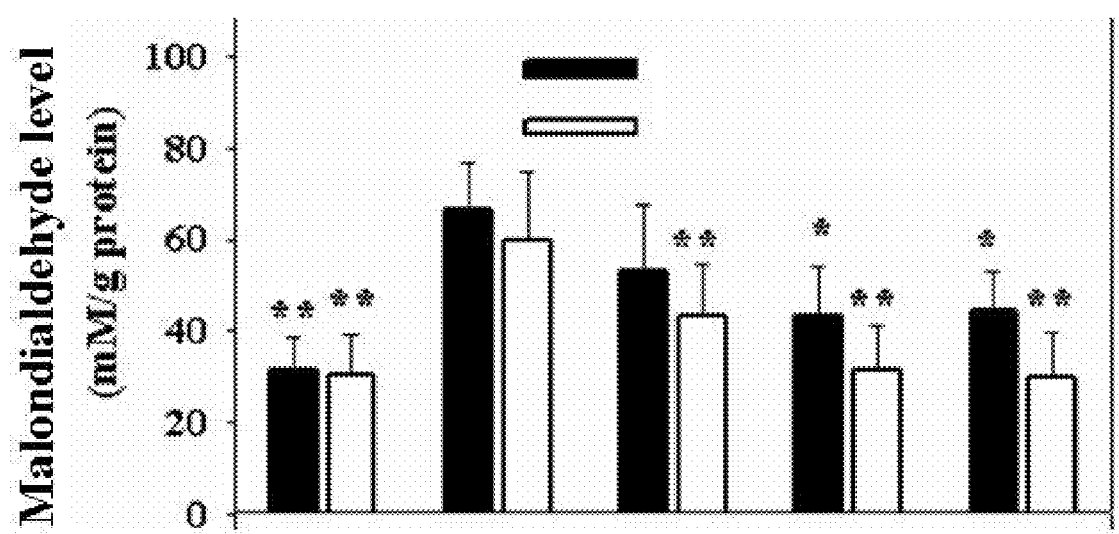
FIG. 8 is an influence diagram showing effect of RMR on the formation of MDA activity in the hippocampus and cortex of Aβ40-infused rats.

The effects of RMR administration on MDA levels of cortex and hippocampus are shown in FIG. 8. MDA levels are significantly increased by 95.3% and 112% in cortex and hippocampus, respectively, through Aβ infusion; but the MDA increase would be remarkably reversed with dose-response by increasing the dosage of RMR.

Figure 9:
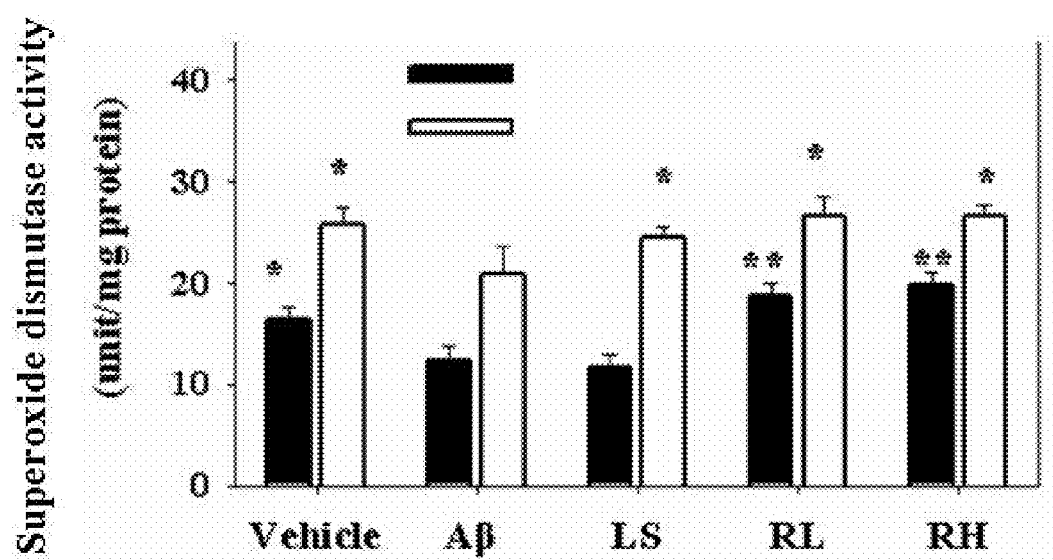
FIG. 9 is an influence diagram showing effect of RMR on the formation of superoxide dismutase (SOD) activity in the hippocampus and cortex of Aβ40-infused rats.

RL and RH groups also showed similar neuroprotective effects on superoxide dismutase (SOD) activity of cortex and hippocampus as shown in FIG. 9. Although SOD activity of cortex and hippocampus were reduced by Aβ infusion by 19.8% and 25.2%, respectively, RL and RH groups exhibited a significant increase in Aβ-reduced SOD activity by 27.2% and 52.7% in cortex and hippocampus with one-fold dosage RMR and by 27.2% and 60.9% in cortex and hippocampus with fivefold dosage RMR.

In view of the foregoing, the rats in the experiment have serious oxidative stress damage in cortex and hippocampus. The oxidative stress damage can be improved by daily RMR dietary with dose-response and better effect than lovastatin group. Anti-oxidant compounds that are extracted from *Monascus*-fermented products include dimerumic acid, tannin, phenol, monounsaturated fatty acid and sterols (Aniya et al. 1999; Wang et al. 2006).

Therefore, the invention indicates that anti-oxidant compounds are able to be selected from either of the following compounds: dimerumic acid, tannin, phenol, monounsaturated fatty acid, sterols and superoxide dismutase (SOD).

Figure 10:
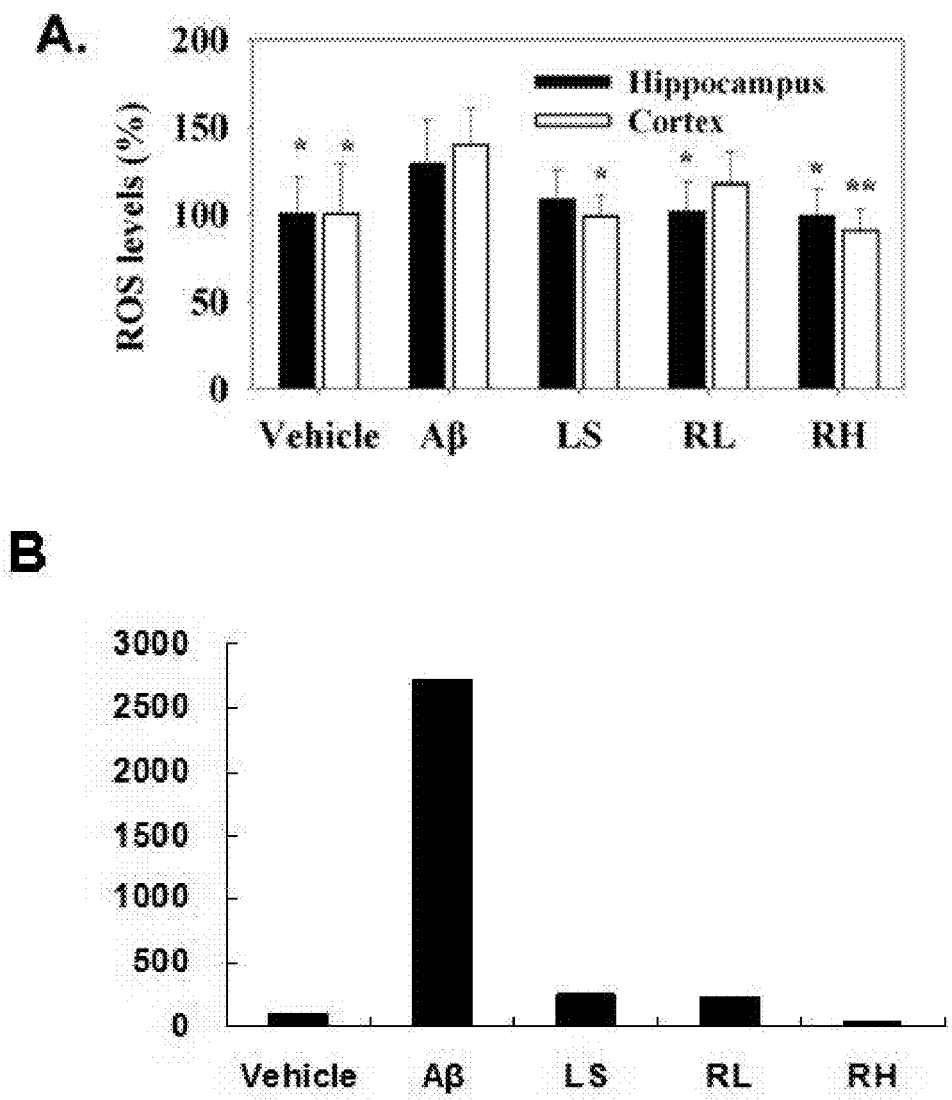
FIGS. 10-A & 10-B are diagrams showing effects of RMR on the formation of ROS in the hippocampus and cortex and iNOS expression of Aβ40-infused rats.

The experiment showed that the results of reactive oxygen species (ROS) levels in cortex and hippocampus as shown in FIG. 10-A. Aβ infusion significantly stimulates the increase of ROS levels in cortex and hippocampus by 39.8% and 28.7% (p<0.05). However, daily administration with RMR in RL and RH groups remarkably reduced Aβ-induced ROS levels in cortex and hippocampus by 16.0% (p<0.05) and 21.2% (p<0.05), respectively, in RL group and by 35.4% (p<0.01) and 21.3% (p<0.05), respectively, in RH group. The decrease in ROS levels by 29.3% in cortex and by 15.7% (p<0.05) in hippocampus were also found in the lovastatin group. The iNOS expression in hippocampus was shown in the immunohistochemical stain in FIG. 10-B. Aβ infusion resulted in a significant increase of iNOS expression, but the expression would be inhibited in the RL and RH groups. Importantly, iNOS expression of hippocampus in RL and RH groups is lower than that in the lovastatin group. The experiment results also showed that the anti-inflammation effect of lovastatin group is lower than that of RL and RH groups with dietary onefold and fivefold dosage RMR.

The significant decrease in ROS levels in cortex and hippocampus can be seen with dose response in the RMR administration groups. Although lovastatin has been used to lower Aβ-induced inflammation response in cell model, the neuroprotective effect of lovastatin has never been used to ameliorate the impairment of memory ability in Aβ-induced AD rat model according to our information. In this study, lovastatin administration also showed a significant decrease in ROS levels and iNOS expression compared with the Aβ group, but the effect was less than in the RL and RH groups. This is not the first report of the anti-inflammatory ability of RMR, the anti-inflammatory metabolites of RMR have been reported including various forms of monacolins; six azaphilones: monascin, ankaflavin, rubropunctatin, monascorburin, rubropunctamine and monascorburamine; two furanoisophthalides: xanthomonasin A and xanthomonasin B; and two amino acids: (+)-monascumic acid and (−)-monascumic acid (Schubert et al. 1995). It is clear that monacolin K is not the only functional metabolite repressing the Aβ-induced inflammation response. Another experiment (Akihisa et al 2005) showed that red mold rice repressed inflammation response induced by 12-O-tetradecanoylphorbol-13-acetate (TPA), the research also proved that major anti-inflammation agents are chemical compounds of azaphilones and furanoisophthalides. The results from this study and related researches regarding RMR against inflammation suggest that RMR repressing Aβ-induced inflammation response mainly results from the coordination mechanism collectively worked by monacolin K and other anti-inflammation agents.

Accordingly, the invention provides inflammation agents, which is able to be selected from the following compounds of γ-aminobutyric acid (GABA), monascin, ankaflavin, rubropunctatin, monascorburin, rubropunctamine, monascorburamine, xanthomonasin A, xanthomonasin B, (+)-monascumic acid and (−)-monascumic acid.

Figure 11:
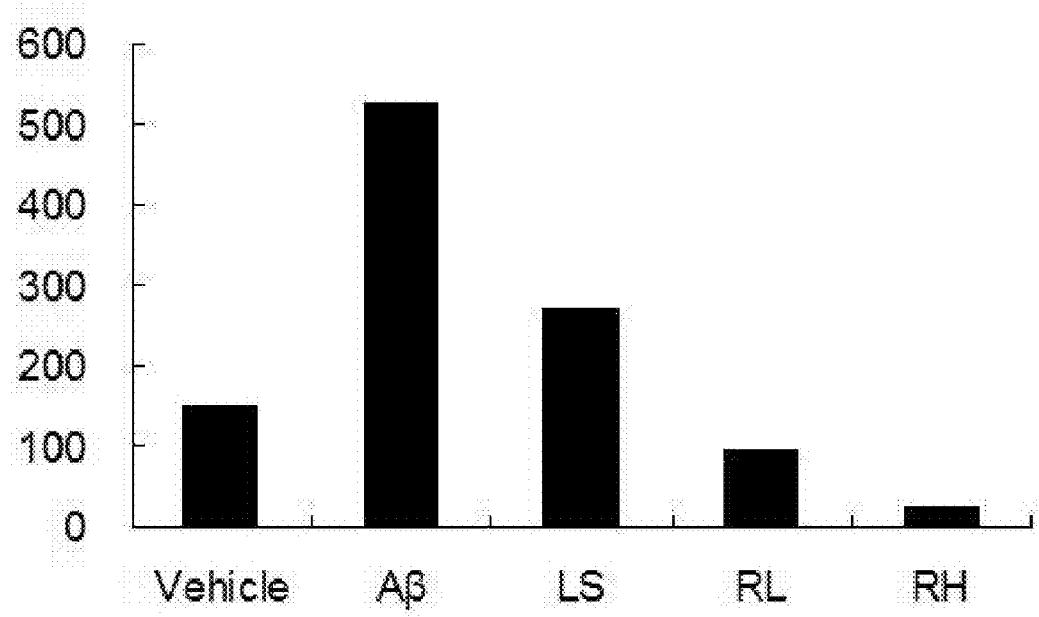
FIG. 11 is a diagram showing effect of RMR on the Aβ40 accumulation in the hippocampus of Aβ40-infused rats.

During the experiment, Aβ40 was continuously infused for 28 days into the brain in hippocampus of the rats. The results in FIG. 11 showed that Aβ40 accumulation in hippocampus of the Aβ group was higher than that in the vehicle group. It is known from the foregoing results and researches that Aβ40 infusion will cause oxidative stress and inflammation response in the brain, and progressively cause Aβ40 accumulation. More Aβ40 accumulation will cause more serious oxidative stress and inflammation response, so as to continuously aggravate brain damage in a vicious circle. Lovastatin has the effect of inhibiting Aβ40-induced inflammation response, but is weaker against oxidative stress. It is found from the experiment results that Aβ40 content of LS group in hippocampus was slightly lower than that of Aβ group; however, there was significant Aβ40 accumulation in the brain. The RL group and RH group with dietary dose of RMR had less Aβ40 accumulation in hippocampus than the Aβ group. The main reason why red mold rice is able to reduce Aβ40 accumulation in hippocampus lies in the ability of inhibiting oxidative stress and inflammation response. Aβ40-infused rats were not influenced by Aβ40 accumulation due to oxidative inflammation agents, so that Aβ40 was unable to cause damage to the brain so as to effectively improve the memory and learning ability.

Monacolins, anti-inflammation agents and anti-oxidant compounds included in the composition and method for the treatment of Alzheimer's disease of the invention are extracted from red mold rice (RMR) to improve existing symptoms or slow Alzheimer's disease. In the first embodiment of the invention, the minimum content of monacolins in 1 g of the composition is at least greater than 100 μg, the minimum content of anti-oxidant compounds in 1 g of the composition is at least greater than 40 μg, and the minimum content of anti-inflammation agents in 1 g of the composition is at least greater than 10 μg, wherein the weight ratio of the monacolins, anti-inflammation agents and anti-oxidant compounds is 40:2:1 as shown in the first embodiment to achieve the best effectiveness. In addition, the weight ratio of the monacolins, anti-inflammation agents and anti-oxidant compounds is in a range from 10:4:1 to 90:2:1 and the composition of the invention is able to be applied to in various forms of pastils, capsules, powder, beverage, etc.

Moreover, in the second embodiment of the invention, the composition comprising the minimum content of monacolins in 1 g of the composition is at least greater than 200 μg and the minimum content of anti-inflammation agents in 1 g of the composition is at least greater than 60 μg; wherein the weight ratio of the monacolins and the anti-inflammation agents is 10:1 as shown in the second embodiment to achieve the best effectiveness; in addition, the weight ratio of the monacolins and the anti-inflammation agents is in a range from 10:3 to 45:1 and the composition in the second embodiment of the invention is proved to achieve the same effect as in the first embodiment of the invention. In the second embodiment of the invention, the composition comprising both monacolins and anti-inflammation agents is able to be used for the treatment of Alzheimer's disease without causing noticeable side effects and applied in various forms of pastils, capsules, powder, beverage, etc. in the treatment of Alzheimer's disease.

Anti-inflammation agents in red mold rice (RMR) is γ-aminobutyric acid (GABA), red mold rice is regarded as natural food and is fermented and extracted through specific methods without causing side effects to human bodies. Therefore, RMR applications for the treatment of Alzheimer's disease only generate significant effectiveness without causing side effects on patients like general pharmaceuticals.

Figures 1, 12:
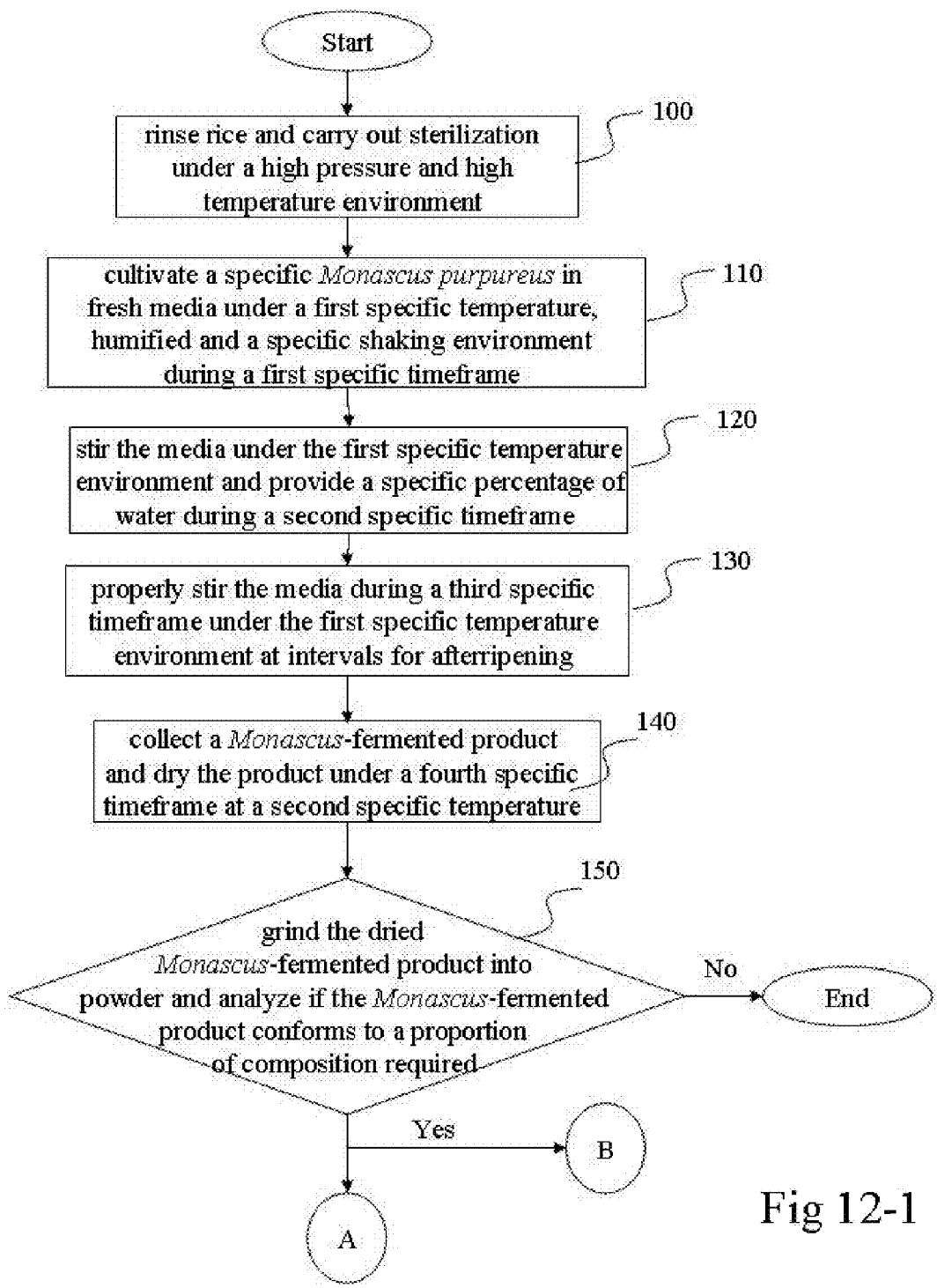
Figures 2, 12:
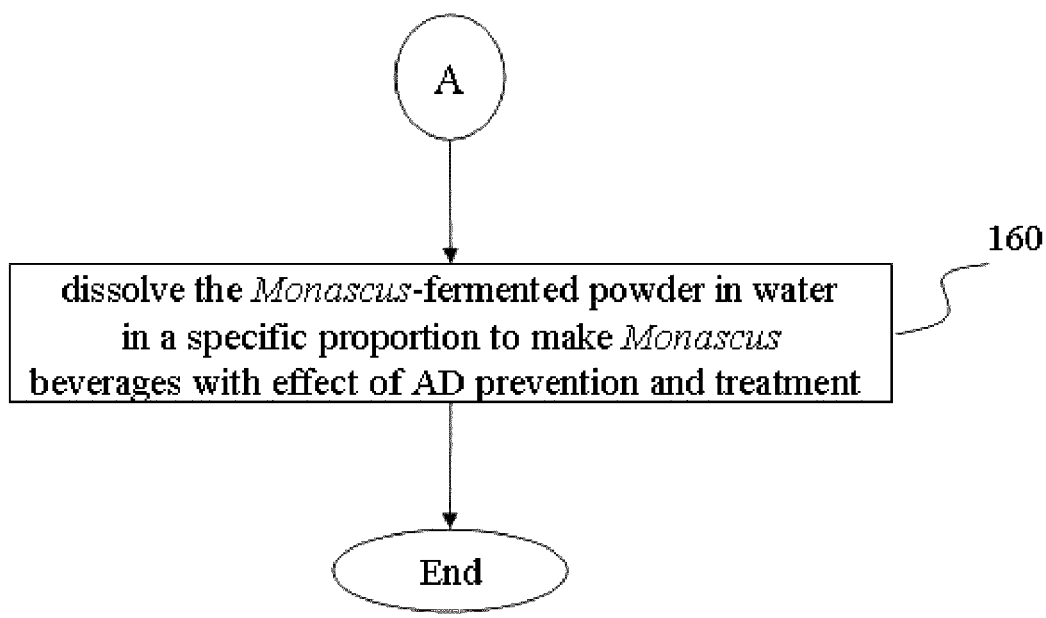
Figures 3, 12:
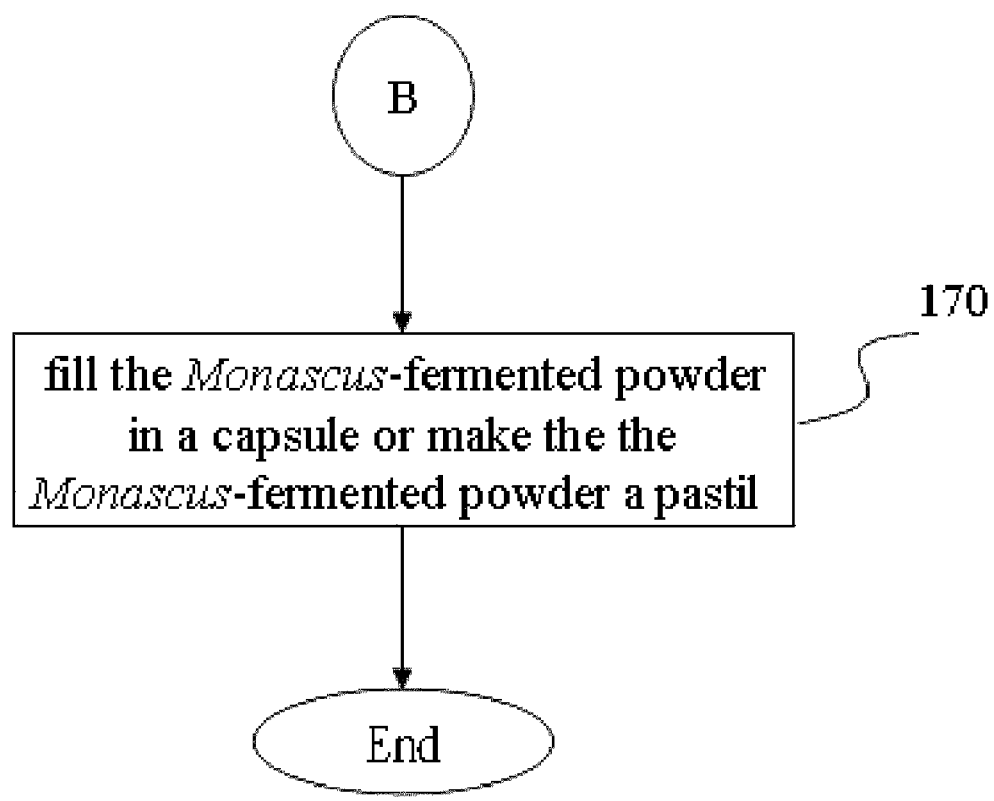

With reference to FIGS. 12-1~12-3, the invention provides a method for the treatment of Alzheimer's disease, the method comprises the following steps:

First of all, the step is to rinse rice and carry out sterilization under a high pressure and high temperature environment (step 100); the rice is long-grain rice (Oryza sativa L., Japonica) purchased from a local supermarket in Taiwan to be used for RMR production under solid-state cultivation and the aforementioned high pressure and high temperature environment means under the environment at 121° C. by the pressure of 1 kg/cm$^2$. The second step is to cultivate a specific Monascus purpureus in fresh media under a first specific temperature, humidified and a specific shaking environment during a first specific timeframe (step 110), wherein the Monascus purpureus in fresh media means at least 5 g of the rice is soaked in 100 mL of sterile distilled water, the first specific timeframe is after 48 hours and the first specific temperature is maintained at 30° C., the specific shaking environment is maintained at a rotational speed between 100 and 150 revolutions per minute (rpm); in other words, the Monascus purpureus is cultivated in the media and maintained in an environment at a temperature of 30° C., a rotational speed 125 rpm and after 48 hours the cultivation is completed for collection. 500 g of solid-state cultivation is then collected, the Monascus is immersed in water for 6~8 hours, filtered by cotton cloth and placed on a cloth in a plate for sterilization (121° C., 20~25 min) Another sterilization (121° C., 20 min) is then carried out after 100 mL of water sprinkling. After cooling, another Monascus cultivation is carried out by placing Monascus in solid-state media (5%). Subsequently, the step is to sufficiently stir the media under the first specific temperature environment and provide a specific percentage of water during a second specific timeframe (step 120), wherein the second specific timeframe means within 72 hours, the specific percentage of water means 20% of sterile distilled water is supplemented; in other words, the Monascus is cultivated in a thermostated container at 30° C. by way of stirring the media every 24 hours within 72 hours and supplementing with 20% of sterile distilled water. The next step is to properly stir the media during a third specific timeframe under the first specific temperature environment at intervals for afterripening (step 130), wherein the afterripening is the formation stage of metabolites and the third specific timeframe is within 96 hours. The fixed intervals are equal to every 10 hours. That is, the Monascus media is properly stirred every 10 hours within a total of 96 hours. Subsequently, after fermentation, the step is to collect a Monascus-fermented product and dry the product under a fourth specific timeframe at a second specific temperature (step 140), wherein the fourth specific timeframe means within 24 hours and the second specific temperature is maintained at the temperature range of 55-60° C. This step is to collect Monascus and carry out the procedure of drying the Monascus-fermented product for 24 hours at 60° C. The next step is to grind the dried Monascus-fermented product into powder and analyze if the Monascus-fermented product conforms to a proportion of composition required (step 150), wherein the proportion of composition required means the composition comprising monacolins, anti-inflammation agents and anti-oxidant compounds at the effective weight ratios ranged from 10:4:1 to 90:2:1. If the Monascus-fermented powder does not conform to the proportion of composition required, the process is ended by failure. When the Monascus-fermented powder conforms to the proportion of composition required in the invention for the treatment of AD, there are step A and step B to follow as shown in FIGS. 12-2 and 12-3. Following step A, the final step is to dissolve the Monascus-fermented powder in water in a specific proportion to make Monascus beverages with effect on AD treatment (step 160) and the process is completed. The specific proportion is between 1.0% and 4.0%.

Following step B, the final step is to fill the *Monascus*-fermented powder in a capsule or make the the *Monascus*-fermented powder a pastil (step 170). The method of the invention is then completed.

The experiment for the invention is carried out through conventional media for *Monascus* production under solid-state cultivation, the koji dish size is 20 (L)×30 (W)×5 cm (H) and a cloth is placed on the bottom of the media for easily stirring and maintaining the humidity, there is another cloth on the top for separation of external contamination and maintaining the moisture of *Monascus* during fermentation. The cultivation is carried out in an opening space. Consequently, the composition of the invention through the method proposed herein is able to be applied to in various forms of pastils, capsules, powder, beverage, etc.

To further explore the prevention and treatment effects of *Monascus*-fermented powder and drinks (NTU568-RMR), more step-through latency and memory and learning ability experiments were carried out on Aβ40-infused rats, using apparatus shown in FIGS. 1 and 3, under conditions described above. In these additional experiments, different groups of rats were fed with NTU568-RMR at different starting times as early as 14 days before Aβ40 infusion, and for different lengths.

Figure 13:
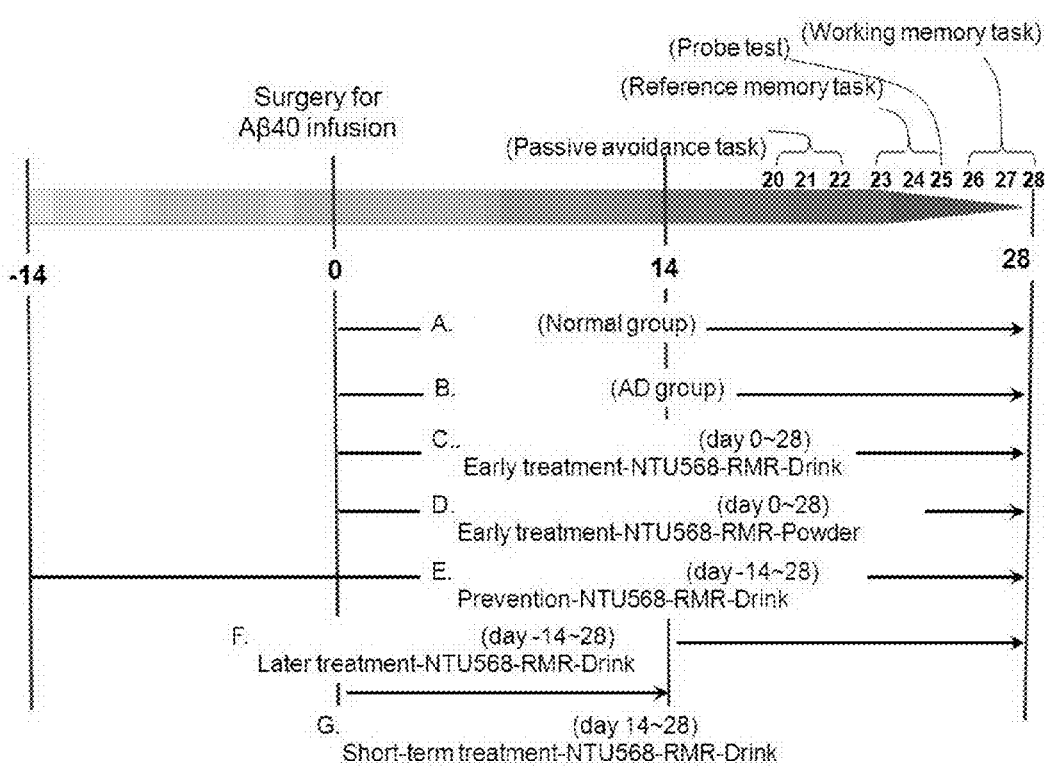
FIG. 13 is flowchart showing the method of feeding TU568 red mold rice (RMR) and Aβ40-infusion to different groups of rats. Group A is the normal group for comparison purpose, where the rats received surgery but no Aβ40-infusion. Group B is the Alzheimer control group, with surgery, Aβ40-infusion, and no RMR feeding. Group C is the early treatment group, where RMR drinks were fed to the rats from day 1 to day 28. Group D is another early treatment group, where RMR powders were fed to the rats from day 1 to day 28. Group E is the prevention group, where RMR drinks were fed to the rats from day-14 (14 days before the surgery and Aβ40-infusion) to day 28. Group G is short-term treatment group, where RMR drinks were fed to the rats from day 1 to day 14. Group F is later treatment group, where RMR drinks were fed to the rats from day 14 to day 28.

FIG. 13 shows a flowchart of feeding TU568 red mold rice (RMR) and Aβ40-infusion to different groups of rats. Group A is the normal group for comparison purpose, where the rats received surgery but no Aβ40-infusion. Group B is the Alzheimer control group, with surgery, Aβ 40-infusion, and no RMR feeding. Group C is the early treatment group, where RMR drinks were fed to the rats from day 1 to day 28. Group D is another early treatment group, where RMR powders were fed to the rats from day 1 to day 28. Group E is the prevention group, where RMR drinks were fed to the rats from day-14 (14 days before the surgery and Aβ40-infusion) to day 28. Group G is short-term treatment group, where RMR drinks were fed to the rats from day 1 to day 14. Group F is later treatment group, where RMR drinks were fed to the rats from day 14 to day 28.

The experiment results show improvements in memory and learning ability for rats that were fed with NTU568-RMR, when compared to the control group that were not fed with the RMR. The improvement in memory, study ability, and reduction of Aβ40 stain in brain correlates with the length of RMR feedings. Specifically, the prevention group rats shows a significant 31.1% improvement in memory and study ability, compared to the later treatment group; and a 22.9% improvement compared to the short-term treatment group ($p<0.05$).

In addition, the rats in later term treatment group, when compared to the short-term treatment group, showed a worse study ability improvement and more precipitation of Aβ40 in brain. This result indicates the more severe damage and oxidation in brain along with the accumulation of Aβ40 precipitation.

Moreover, experimental results show that stop or delay in feeding of RMR increases Aβ40 precipitation in the hippocampus and cortex region of of rats' brain, leading to more severe damage of memory and study ability.

Figure 14:
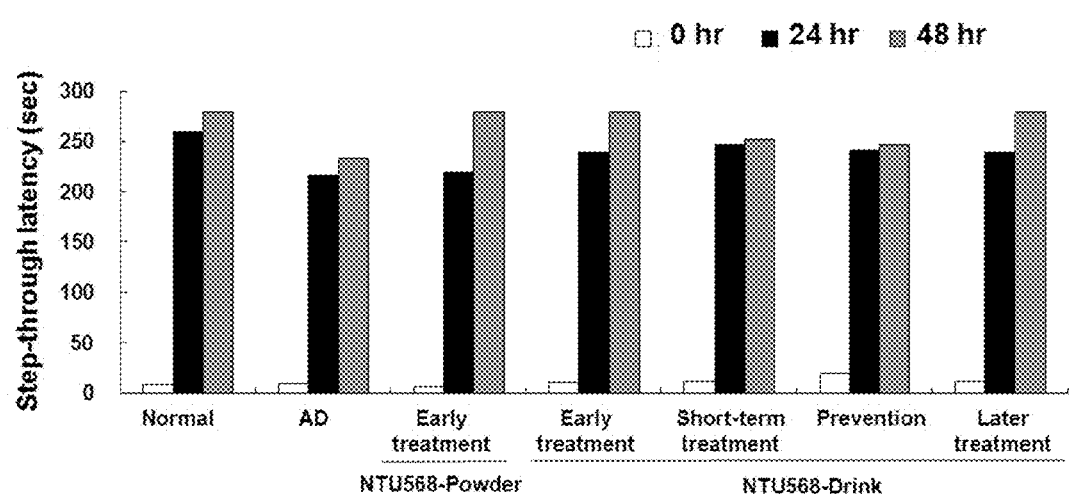
FIG. 14 is a statistical chart showing the effect of RMR on step-through latency of multiple-trial passive avoidance task in the rats from a light chamber into a dark chamber, at 0 hr, 24 hr, and 48 hr.

As shown in FIG. 14, which is a statistical chart showing the effect of RMR on step-through latency of multiple-trial passive avoidance task in the rats from a light chamber into a dark chamber (see the apparatus set up and experimental condition as explained in the results shown in FIG. 2 above), at 0 hr, 24 hr, and 48 hr, feeding of NTU568 RMR improves memory and study ability of rats, which allow the rats to stay for longer time in the light chamber at 24 hr and 48 hr.

Figure 15:
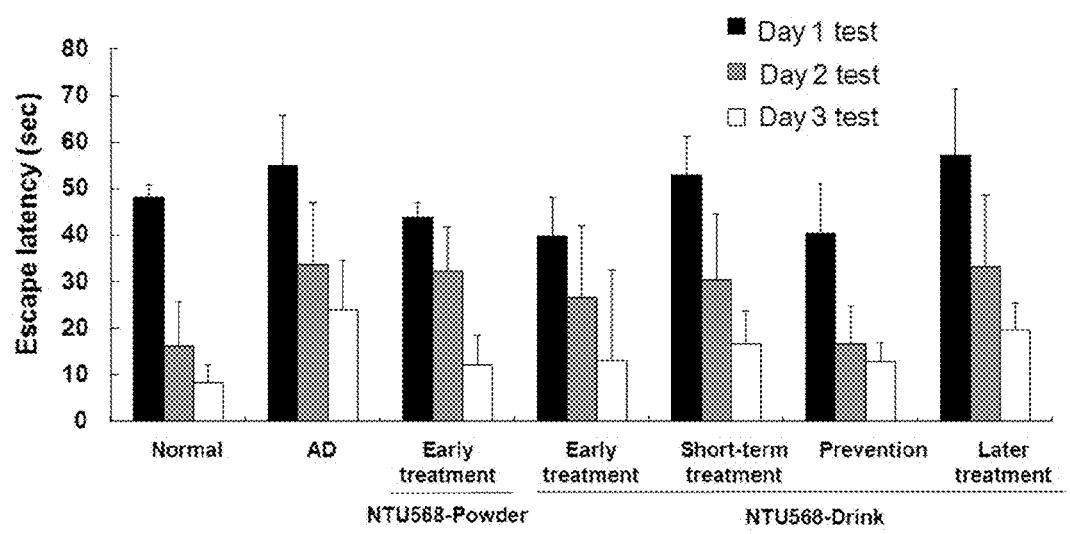
FIG. 15 is a chart showing effect of RMR on performance of the memory and learning ability of the Aβ40-infused rats in the training trials of working memory task, when water maze was used, at day 1, day 2, and day 3.

The results of FIG. 15 are obtained by using water maze apparatus described in FIG. 3 and corresponding texts. Similar to FIG. 4 but with more rats groups data, FIG. 15 is a chart showing effect of RMR on performance of the memory and learning ability of the Aβ40-infused rats in the training trials of working memory task, when water maze was used, at day 1, day 2, and day 3. As can be seen from the figure, the rats in the prevention group can find platform in a much shorter time on day 2 and day 3.

Figure 16:
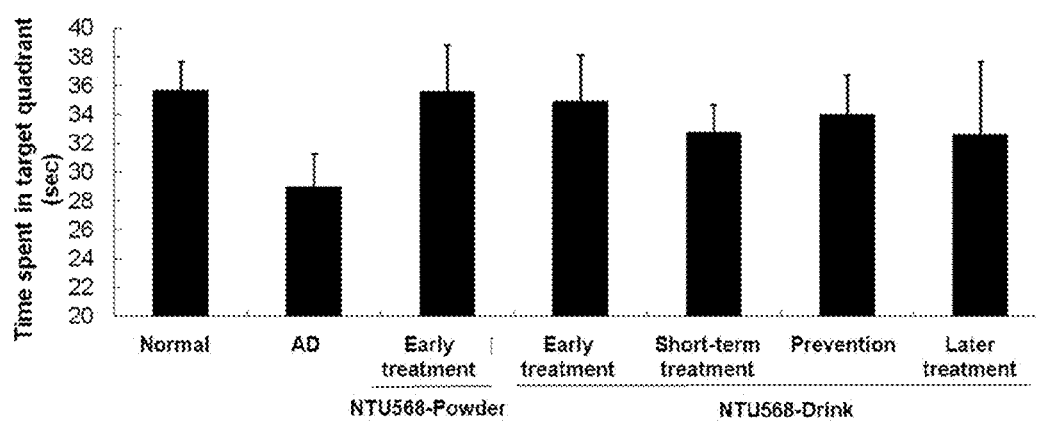
FIG. 16 shows influence diagrams regarding effects of RMR on performance of the memory and learning ability of the Aβ40-infused rats in the training trials of reference memory task and probe test, measured by the rats' swimming time spent in target quadrant of water maze.
Figure 17:
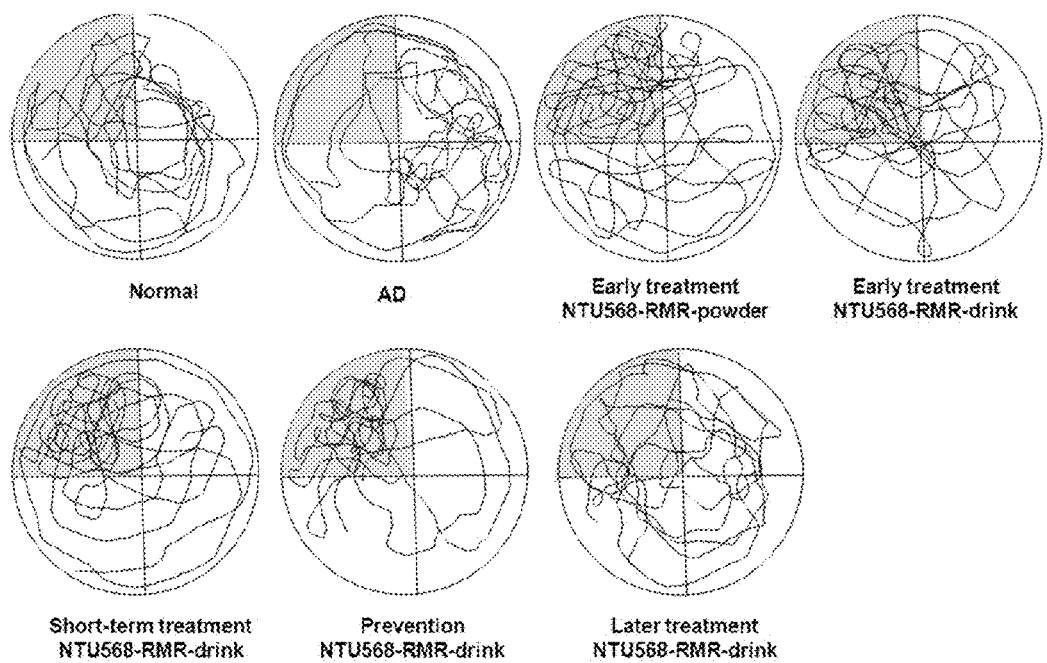
FIG. 17 shows influence of NTU 568 RMR on the swimming paths of Aβ40-infused rats inside water maze.

FIGS. 16 and 17 show influence diagrams regarding effects of RMR on performance of the memory and learning ability of the Aβ40-infused rats in the training trials of reference memory task and probe test, measured by the rats' swimming time spent in target quadrant of water maze. After the platform is removed from water maze, the time that rats started from a starting point of the apparatus of water maze to search the escape platform is regarded as the index for evaluation of the reference memory task. The longer the rats wandered to look for platform in the region where the platform was placed, the better memory the rats had. The experiment results show that the AD group of rats has the worst memory and spent the least time in the quadrant. Among all other groups, the prevention group rats shows a significant 31.1% improvement in memory and study ability, compared to the later treatment group; and a 22.9% improvement compared to the short-term treatment group ($p<0.05$). This result proves the effect of prevention, by consuming RMR, in the rats' improvement of memory and study ability.

Figure 18:
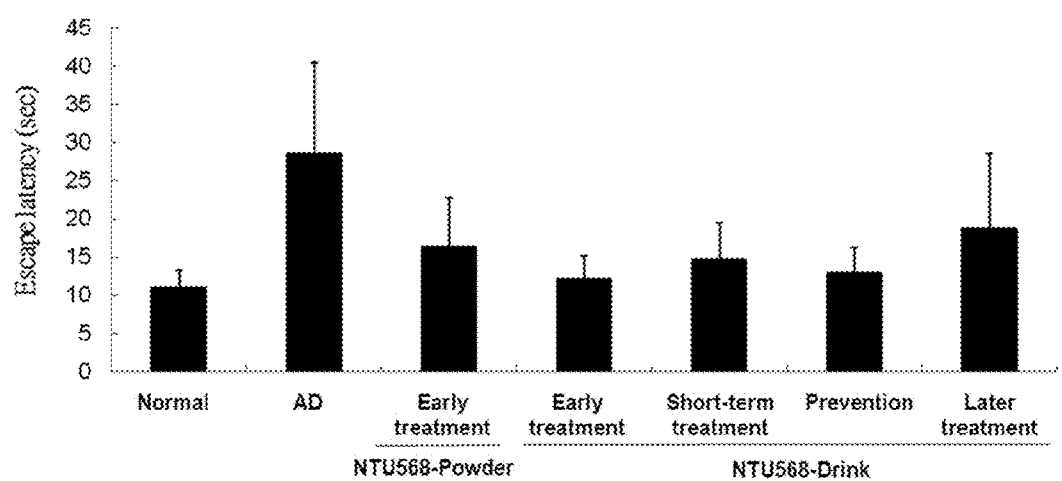
FIG. 18 is a chart showing effect of RMR on performance of the memory and learning ability of the Aβ40-infused rats in the training trials of working memory task, measured by the time rats spent in finding the platforms after the platforms' locations were moved.

FIG. 18 is a chart showing effect of RMR on performance of the memory and learning ability of the Aβ40-infused rats in the training trials of working memory task, measured by the time rats spent in finding the platforms after the platforms' locations were moved. After the platform was removed, the AD group rats spent the longest time to find out the new location of platform. Both the prevention group and the early treatment group showed shortened time in finding platform. The later term treatment group also showed improvements, but not as good as other treatment groups.

Figure 19:
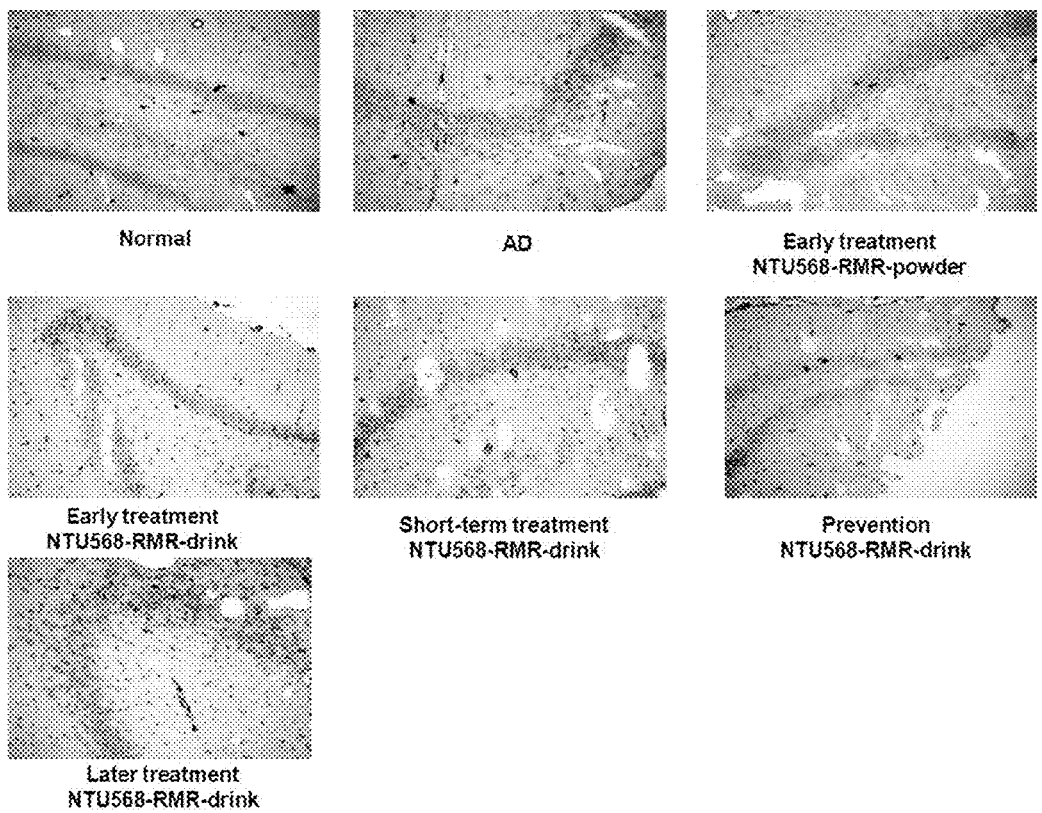
FIG. 19 shows effect of RMR on the precipitation of Aβ40 in the hippocampus and cortex of rats. The stained brown dots indicate precipitation.

FIG. 19 shows effect of RMR on the precipitation of Aβ40 in the hippocampus and cortex region of rats' brain. The stained brown dots indicate precipitation of Aβ40. The rats in the later term treatment group, when compared to the short-term treatment group, showed a worse study ability improvement and more precipitation of Aβ40 in brain. This result indicates the more severe damage and oxidation in brain along with the accumulation of Aβ40 precipitation. Stop or delay in feeding of RMR increases Aβ40 precipitation in the hippocampus and cortex region of rats' brain, leading to more severe damage of memory and study ability. In contrast, consuming NTU568-RMR for long periods of time can prevent formation of Aβ in brain and the precipitation of Aβ40, thus decrease the accumulation of Aβ40 in brain and reduce the correlated memory problem.

New characteristics and advantages of the invention covered by this document have been set forth in the foregoing description. It is of course to be understood, however, that this disclosure is, in many respects, only illustrative. Changes may be made in details without exceeding the scope of the invention by those who are skilled in the art under the doctrine of equivalents, such as monacolins, anti-inflammation agents and anti-oxidant compounds, or other composition against Alzheimer's disease (not limit to red mold rice extracts). The scope of the invention is, of course, defined in the language in which the appended claims are expressed.

While various embodiments in accordance with the present invention have been shown and described, it is understood that the invention is not limited thereto. The present invention

We claim:

1. A method for making *Monascus*-fermented powder product suitable for the treatment of Alzheimer's disease and reduction of development in Alzheimer's related symptoms, comprising the following steps:
   (a) rinsing rice and carrying out sterilization under a specific pressure and a specific temperature environment on the rice to form a fresh medium;
   (b) cultivating *Monascus purpureus* in said fresh medium in a specific shaking environment under a first specific temperature and a specific humidity during a first specific timeframe;
   (c) stirring the medium under the first specific temperature and the specific humidity environment and providing a specific percentage of water during a second specific timeframe;
   (d) stirring the medium during a third specific time frame under the first specific temperature and the specific humidity environment at intervals;
   (e) collecting a *Monascus*-fermented product and drying the product under a fourth specific timeframe at a second specific temperature;
   (f) grinding the dried *Monascus*-fermented product into powder and analyze if the *Monascus*-fermented product conforms to a required proportion, as having one or more monacolins, one or more anti-inflammation agents and one or more anti-oxidant compounds at a weight ratio in a range from 10:4:1 to 90:2:1; and
   (g) filling the *Monascus*-fermented powder obtained in step (f) in a capsule or making the *Monascus*-fermented powder into a pastil,
   wherein:
      the first specific temperature is maintained at 30° C.;
      the second specific temperature ranges between 55-60° C.;
      the first specific timeframe is at least 48 hours;
      the second specific timeframe is 72 hours;
      the third specific timeframe is 96 hours; and
      the fourth specific timeframe is 24 hours.

2. The method of claim 1, wherein the rice is *Oryza sativa* L., Japonica.

3. The method of claim 1, wherein the specific pressure is 1 kg/cm$^2$ and the specific temperature environment is 121° C.

4. The method of claim 1, wherein the fresh media comprises at least 5 g of the rice soaked in 100 mL of sterile distilled water.

5. The method of claim 1, wherein the specific shaking environment is maintained at a rotational speed between 100 and 150 revolutions per minute (rpm).

6. The method of claim 1, wherein the specific percentage of water means 20% of sterile distilled water.

7. The method of claim 1, wherein the intervals are equal to every 10 hours.

8. The method of claim 1, wherein the monacolins, the anti-inflammation agents and the anti-oxidant compounds have a weight ratio of 40:2:1.

9. A method for making *Monascus*-fermented beverage product suitable for the treatment of Alzheimer's disease and reduction of development in Alzheimer's related symptoms, comprising the following steps:
   (a) rinsing rice and carrying out sterilization under a specific pressure and a specific temperature environment on the rice to form a fresh medium;
   (b) cultivating *Monascus purpureus* in said fresh medium in a specific shaking environment under a first specific temperature and a specific humidity during a first specific timeframe;
   (c) stirring the medium under the first specific temperature and the specific humidity environment and providing a specific percentage of water during a second specific timeframe;
   (d) stirring the medium during a third specific time frame under the first specific temperature and the specific humidity environment at intervals;
   (e) collecting a *Monascus*-fermented product and drying the product under a fourth specific timeframe at a second specific temperature;
   (f) grinding the dried *Monascus*-fermented product into powder and analyze if the *Monascus*-fermented product conforms to a required proportion, as having one or more monacolins, one or more anti-inflammation agents and one or more anti-oxidant compounds at a weight ratio in a range from 10:4:1 to 90:2:1; and
   (g) dissolving the *Monascus*-fermented powder obtained in step (f) in water in a specific proportion to form *Monascus* beverages,
   wherein:
      the first specific temperature is maintained at 30° C.;
      the second specific temperature ranges between 55-60° C.;
      the first specific timeframe is at least 48 hours;
      the second specific timeframe is 72 hours;
      the third specific timeframe is 96 hours; and
      the fourth specific timeframe is 24 hours.

10. The method of claim 9, wherein the specific proportion in step (g) is the proportion of the *Monascus*-fermented powder to water, and the specific proportion is between 1.0% and 4.0%.

* * * * *